United States Patent [19]

Hata et al.

[11] Patent Number: 4,690,816

[45] Date of Patent: Sep. 1, 1987

[54] TYPE SOFT CAPSULE

[75] Inventors: Takehisa Hata, Mukou; Nobuto Kanagawa, Kyogo; Takashi Morishita; Toshiyuki Suzuki, both of Osaka, all of Japan

[73] Assignees: Fujisawa Pharmaceutical Co., Ltd.; Morishita Jintan Co., Ltd., both of Osaka, Japan

[21] Appl. No.: 798,360

[22] Filed: Nov. 18, 1985

Related U.S. Application Data

[63] Continuation of Ser. No. 534,109, Sep. 20, 1983, abandoned.

[30] Foreign Application Priority Data

Sep. 20, 1982 [JP] Japan ................................ 57-164706

[51] Int. Cl.$^4$ .............................................. A61K 9/48
[52] U.S. Cl. ...................................... 424/456; 514/962
[58] Field of Search ................... 424/37; 514/774, 786, 514/277

[56] References Cited

U.S. PATENT DOCUMENTS

| 2,183,053 | 12/1939 | Taylor | 424/37 |
| 2,643,209 | 6/1953 | Goett | 424/37 |
| 2,691,619 | 10/1954 | Bavley | 424/37 |
| 2,987,444 | 6/1961 | Allardice | 424/37 |
| 3,312,594 | 4/1967 | Norman et al. | 424/360 |
| 3,344,028 | 9/1967 | Personeus et al. | 424/360 |
| 3,445,563 | 5/1969 | Clegg et al. | 424/37 |
| 3,676,363 | 7/1972 | Mosier | 424/37 |
| 4,428,927 | 1/1984 | Ebert et al. | 424/37 |

FOREIGN PATENT DOCUMENTS

| 799450 | 11/1968 | Canada | 424/37 |
| 1037073 | 7/1955 | Fed. Rep. of Germany | 424/360 |
| 76774 | 9/1969 | Fed. Rep. of Germany | 424/360 |
| 4629745 | 12/1969 | Japan | 424/360 |
| 56-97220 | 12/1979 | Japan | 424/360 |
| 58-62120 | 10/1981 | Japan | 424/360 |

*Primary Examiner*—Shep K. Rose
*Attorney, Agent, or Firm*—Oblon, Fisher, Spivak, McClelland & Maier

[57] ABSTRACT

A soft capsule which is prepared by wrapping an oily substance which is a member selected from the group consisting of tricaprylic acid glyceride and sesame oil, with a gelatin film containing sodium picosulfate.

2 Claims, No Drawings

TYPE SOFT CAPSULE

This application is a continuation of application Ser. No. 534,109, filed Sept. 20, 1983, now abandoned.

This invention relates to a new type of soft capsule which comprises wrapping an oily substance with a film containing a water-soluble medicinal substance.

The object of this invention is to provide a new type soft capsule which can be applied to a water-soluble medicinal substance.

It has been known to prepare soft capsules by wrapping an oily substance containing a medicinal substance with gelatin film.

When the medicinal substance is water-soluble, soft capsules have been prepared by wrapping a suspension of the water-soluble medicinal substance in oil with a gelatin film.

According to this method, however, it is inevitable that the quality of the capsule deteriorates in the equality of the content of the medicinal substance in each capsule, because it is difficult to maintain the level of equality of suspension to be filled in each capsule during the preparation thereof.

This tendency becomes more and more remarkable as the content of the medicinal substance is decreased, and sometimes results in serious problems with the quality of the medicine.

The inventors of this invention have attempted to resolve this kind of problem, and finally got an idea to add the water-soluble medicinal substance to a film. Such an idea could be obtained by breaking down the ordinary knowledge that medicinal substance is contained in an oily phase of a soft capsule. The soft capsule of this invention has a different constitution from the conventional soft capsule defined in pharmacopoeia, and accordingly the soft capsule presented by this invention is called a "new type of soft capsule" in this specification.

The new type soft capsule of this invention can be prepared by wrapping an oily substance with a film containing a water-soluble medicinal substance.

The main component of the film is not restricted, but usually the film consists of gelatin optionally treated with a organic or inorganic acid or alkaline substance. Conventional additives to the film such as coloring agents, plasticizers, antiseptics, wetting agents, solubilizing agents, disintegrants, flavorants, antioxidizing agents, and the like can be optionally added to the film component.

This invention can be applied to a water-soluble medicinal substance which can be dissolved in the film component. In case the medicinal substance cannot be easily dissolved in the film component, a solubilizing agent can optionally be used. Accordingly, the water-soluble medicinal substance of this invention includes not only ones which can be easily dissolved in water, but also ones which can be dissolved in water by using solubilizing agent. The content of the medicinal substance contained in the film can be selected according to a dose of the medicine in a range where the medicinal substance can be dissolved in the film component.

The oily substance to be wrapped by the film as mentioned above may be a conventional one such as vegetable oil (e.g. olive oil, safflower oil, corn oil, sunflower oil, cotton seed oil, tsubaki oil, rice bran oil, soybean oil, sesame oil, wheat germ oil, coconut oil, peanut oil, rape oil, etc.), fish oil (e.g. cuttlefish oil, cod oil, etc.), liver oil (e.g. shark liver oil, cod liver oil, etc.), blubber oil (e.g. seal oil, blue whale oil, etc.), conchiferas oil (e.g. abalone oil, oyster oil, etc.), a mixture of these animal oils, a medicinal oily substance (e.g. liver oil, castor oil, fatty acid glyceride, vitamin E, vitamin A, vitamin K, etc.), polyethylene glycol, or the like.

These oily substances can optionally contain medicinal substances which can be dissolved therein.

The new type soft capsule of this invention can be prepared by a conventional method, and preferably by the method described in the specification of Japanese Patent Publication No. 1067/1978, according to which the new type soft capsule equalized in the weight of the film can be easily prepared.

The new type soft capsule of this invention possesses superior effects as follows. That is, the content of the medicinal substance in each capsule can be easily equalized even though the medicinal substance is water-soluble. And further, the medicinal stbstance can be dissolved in a short time after administration, since the substance is contained in the surface part of the soft capsule.

In addition to the above, beautiful soft capsules can be obtained when both the oily substance and the film are transparent, because the medicinal substance is not suspended in the oily substance but rather is dissolved in the film component.

The method for preparing the new type soft capsule of this invention is explained in more detail in the following Examples.

EXAMPLE 1

(Film Components)

Sodium picosulfate: 1.5 mg,
Gelatin: 7 mg,
D-Sorbitol: 1 mg,
Glycerol: 2 mg,
Ethylparaben: 0.03 mg,
Propylparaben: 0.01 mg,
Reddish coloring agent: q.s.

(Oily Substance)

Tricaprylic acid glyceride: 23 mg,

New type soft capsules with a diameter of 4 mm were prepared by the method described in the specification of Japanese Patent Publication No. 1067/1978 by using the film components and the oily substance in the ratio as described above.

EXAMPLE 2

New type soft capsules were prepared by the method described in the specification of Japanese Patent Publication No. 1067/1978 by using sesami oil instead of tricaprylic acid glyceride in Example 1.

EXAMPLE 3

New type soft capsules were prepared by the method described in the specification of Japanese Patent Publication No. 1067/1978 by using maleic acid chlorpheniramine (2 mg) instead of sodium picosulfate in Example 1.

We claim:

1. A soft capsule which is prepared by wrapping an oily substance which is a member selected from the group consisting of tricaprylic acid glyceride and sesame oil, with a gelatin film containing sodium picosulfate.

2. A soft capsule comprising:
   a film containing gelatin, wherein said gelatin has dissolved therein sodium picosulfate, said film wrapped around a core which consists of tricaprylic acid glyceride,
   said capsule having a diameter of about 4 mm.

* * * * *